(12) United States Patent
Hasegawa et al.

(10) Patent No.: US 8,273,027 B2
(45) Date of Patent: Sep. 25, 2012

(54) ULTRASONIC PROBE

(75) Inventors: Yasunobu Hasegawa, Saitama (JP);
Chiharu Tsukamoto, Saitama (JP)

(73) Assignee: Nihon Dempa Kogyo Co., Ltd., Tokyo (JP)

( * ) Notice: Subject to any disclaimer, the term of this patent is extended or adjusted under 35 U.S.C. 154(b) by 912 days.

(21) Appl. No.: 12/322,018

(22) Filed: Jan. 28, 2009

(65) Prior Publication Data

US 2009/0209860 A1    Aug. 20, 2009

(30) Foreign Application Priority Data

Feb. 19, 2008 (JP) .................. 2008-037650

(51) Int. Cl.
*A61B 8/14* (2006.01)
*G01N 29/24* (2006.01)
(52) U.S. Cl. ......... 600/459; 600/445; 600/446; 600/444
(58) Field of Classification Search .................. None
See application file for complete search history.

(56) References Cited

U.S. PATENT DOCUMENTS

| | | | | |
|---|---|---|---|---|
| 4,186,747 | A | * | 2/1980 | Iinuma ............... 600/444 |
| 4,282,879 | A | * | 8/1981 | Kunii et al. ........... 600/445 |
| 5,317,778 | A | * | 6/1994 | Kudo et al. ........... 15/88.3 |
| 2003/0109786 | A1 | * | 6/2003 | Irioka et al. .......... 600/459 |
| 2005/0288587 | A1 | * | 12/2005 | Roh et al. ........... 600/445 |

FOREIGN PATENT DOCUMENTS

| | | |
|---|---|---|
| JP | 56-018770 | 2/1981 |
| JP | 59-228836 | 12/1984 |
| JP | 61-013942 | 1/1986 |
| JP | 64-015650 | 1/1989 |
| JP | Hei7-38851 | 5/1995 |
| JP | 2003-175033 | 6/2003 |
| JP | 2004-313290 | 11/2004 |
| JP | 2006-346125 | 12/2006 |
| JP | 200880093 | 4/2008 |

* cited by examiner

*Primary Examiner* — Long V. Le
*Assistant Examiner* — Farshad Negarestan
(74) *Attorney, Agent, or Firm* — Edwards Wildman Palmer LLP; Scott D. Wofsy

(57) ABSTRACT

In an ultrasonic probe of the present invention, a probe main body that comprises a flat shaped piezoelectric element group having a plurality of strip shaped piezoelectric elements arranged in a line in the major axis direction, which is the crosswise direction of the piezoelectric elements, is formed and housed within a container main body and sealed therein with a cover. The ultrasonic probe is characterized in that, in order to mechanically and linearly scan the probe main body in the minor axis direction, which is the lengthwise direction of the piezoelectric elements, the probe main body is linearly reciprocated and mechanically scanned in the minor axis direction, by an endless belt that is driven by a drive source via another endless belt linearly in the minor axis direction, while being guided by a pair of linear guides. As a result, sufficient movement stroke of the probe main body in the minor axis direction can be ensured, and by means of a movement mechanism comprising the endless belt, the probe main body can be reciprocated in the minor axis direction to the fullest extent between the inner walls of a sealed container.

6 Claims, 9 Drawing Sheets

ULTRASONIC PROBE

BACKGROUND OF THE INVENTION

1. Technical Field

The present invention relates to an ultrasonic probe (hereunder, referred to as a "minor axis mechanical scanning probe") that mechanically scans a piezoelectric element group in a minor axis direction, in particular, to a minor axis mechanical scanning probe in which the piezoelectric element group is linearly reciprocated in the minor axis direction.

2. Background Art

A minor axis mechanical scanning probe, for example, electronically scans a piezoelectric element group (probe main body) in the major axis direction thereof, and mechanically scans in the minor axis direction thereof, to obtain a three dimensional image (refer to Japanese Examined Patent Publication No. Hei 7-38851, Japanese Unexamined Patent Publication No. 2003-175033, and Japanese Unexamined Patent Publication No 2006-346125).

Such a probe has been brought to practical application because for example wiring (electrical connections) and scanning circuits thereof, can be made simpler, compared for example to a matrix type probe in which piezoelectric elements are arranged in lengthwise and crosswise arrays to be electronically scanned in a two-dimensional direction.

However, in the conventional minor axis mechanical scanning probe, the piezoelectric element group is electronic linear scanned in the minor axis direction in a circular arc. Therefore, so as to follow this circular arc, the ultrasonic wave transmitting/receiving surface of the sealed container also forms a circular arc convex section in the minor axis direction. Moreover, in these conventional examples, the piezoelectric element group is a convex shape (convex-curved surface) in the major axis direction, Therefore, so as to follow this shape, the shape of the sealed container in the major axis direction also forms a convex shape. Consequently, the ultrasonic wave transmitting/receiving surface becomes a convex shape in the minor axis direction and the major axis direction, so that it is entirely convex (mountain shape).

Due to this, there has been a problem in that it is difficult to bring the entire surface of the wave transmitting/receiving surface into contact with a breast (convex section, mountain section), for example when diagnosing a mammary gland of a living body (of a female in particular) with a probe. In the case where the entire surface of the wave transmitting/receiving surface does not come into contact with a breast, attenuation of the ultrasonic waves occurs, and a normal diagnostic image of the living body cannot be obtained.

Moreover, the conventional minor axis mechanical scanning probe scans a living body in a circular arc in the minor axis direction (in the piezoelectric element length direction). Hence there has also been a problem in that lateral resolution becomes rougher when a section of the living body to be scanned is deeper.

Therefore, for example, there has been proposed by the inventor (Yasunobu Hasegawa) of the present application, a minor axis mechanical scanning probe that can be easily brought into contact with a protruding portion of a living body such as breast, and that realizes excellent lateral solution (Japanese Unexamined Patent Publication No. 2008-80093).

This proposed minor axis mechanical scanning probe, as shown in FIGS. 9A and 9B, is configured such that: a plurality of strip shaped piezoelectric elements 102a is arranged in a line in the major axis direction, which is the crosswise direction of the piezoelectric elements 102a, so as to form a flat shaped piezoelectric element group 102; the piezoelectric element group 102 is housed within a sealed container 103 filled with a liquid L that functions as an ultrasonic medium; and the piezoelectric element group 102 is mechanically scanned in the minor axis direction, which is the lengthwise direction of the piezoelectric elements 102a.

According to such a configuration, the piezoelectric element group 102 does not rotate/oscillate in a circular arc in the minor axis direction, but linearly moves (reciprocates) in the minor axis direction. Consequently, the wave transmitting/receiving surface of the sealed container 103 does not have to be made in a convex shape as with the conventional example, and can be made into a flat surface. As a result it can be made easier to fully contact the wave transmitting/receiving surface of the sealed container 103 with a living body such as breast.

Furthermore, since the piezoelectric element group 102 linearly moves (reciprocates) in the minor axis direction, ultrasonic waves from the wave transmitting/receiving surface are irradiated in parallel onto the part to be examined. Consequently, the spacing of the ultrasonic waves is constant even in a deeper part of a living body, and thereby the lateral resolution can be improved while increasing the movement speed of the piezoelectric element group.

Moreover, in this probe, as shown in FIGS. 9A and 9B, the piezoelectric element group 102 is provided on a movable mount 110 via a base 105 and a backing member 105a, and on the surface of the piezoelectric element group 102 there is provided, via an acoustic matching layer 106a, an acoustic lens 106, thereby forming a probe main body 101.

Furthermore, the configuration is such that: on both end sides of the movable mount 110 in the major axis direction, there is provided a pair of leg sections 110a and 110b, and guide shafts 111 are inserted through the pair of leg sections 110a and 110b in the minor axis direction, and supported on side walls 103b of the sealed container 103; a rack 113, in the minor axis direction, is fixed on one of the pair of leg sections 110a and 110b; and a rotating gear (pinion) 114 with an electric motor as a drive source, is meshed with the rack 113. Moreover, the guide shafts 111 passing through in the minor axis direction are provided in the pair of the leg sections 110a and 110b formed in the major axis direction of the movable mount 110 having the piezoelectric element group 102 provided thereon. Therefore the piezoelectric element group 102 can freely reciprocate in the minor axis direction. Here, the rack 113 provided in the minor axis direction on the one leg section 110a of the movable mount 110 is meshed with the rotating gear 114 with the electric motor as a drive source, and is thereby moved (reciprocated).

However, in this proposed minor axis mechanical scanning probe (Japanese Unexamined Patent Publication No. 2008-80093), as shown in FIG. 9B, the rack 113 that meshes with the rotating gear (pinion) 114 requires a length several times that of the rotating gear 114 in order to stably and linearly move the piezoelectric element group 102 in the minor axis direction with guidance of the guide shafts 111. Consequently, before the piezoelectric element group 102 can reach both of the inner walls 103a and 103b of the sealed container 103, both end surfaces of the movable mount 110 are contacted with both of the inner walls 103a and 103b. Therefore, there is a problem in that sufficient movement stroke in the minor axis direction of the probe main body can not be ensured.

A problem to be solved by the present invention is that in order to ensure sufficient movement stroke in the minor axis direction of the probe main body, then with a movement mechanism comprising an endless belt, the probe main body is reciprocated in the minor axis direction to the fullest extent between the inner walls of the container that contains the probe main body, to thereby ensure sufficient movement stroke in the minor axis direction.

SUMMARY OF THE INVENTION

In order to solve the above problem, the present invention is an ultrasonic probe in which a probe main body that comprises a flat shaped piezoelectric element group having a plurality of strip shaped piezoelectric elements arranged in a line in the major axis direction, which is the crosswise direction of the piezoelectric elements, is formed and housed within a container main body, and the probe main body is mechanically scanned in the minor axis direction, which is the lengthwise direction of the piezoelectric elements, and is characterized in that the probe main body is linearly reciprocated in the minor axis direction by a first endless belt that is driven by a drive source.

With such a configuration, it is possible to ensure linear movement (reciprocation) strokes of the probe main body in the minor axis direction to the fullest extent between the inner walls.

DETAILED DESCRIPTION OF THE PREFERRED EMBODIMENT

Hereunder, an embodiment of an ultrasonic probe of the present invention is described, with reference to the accompanying drawings.

Figure 1:
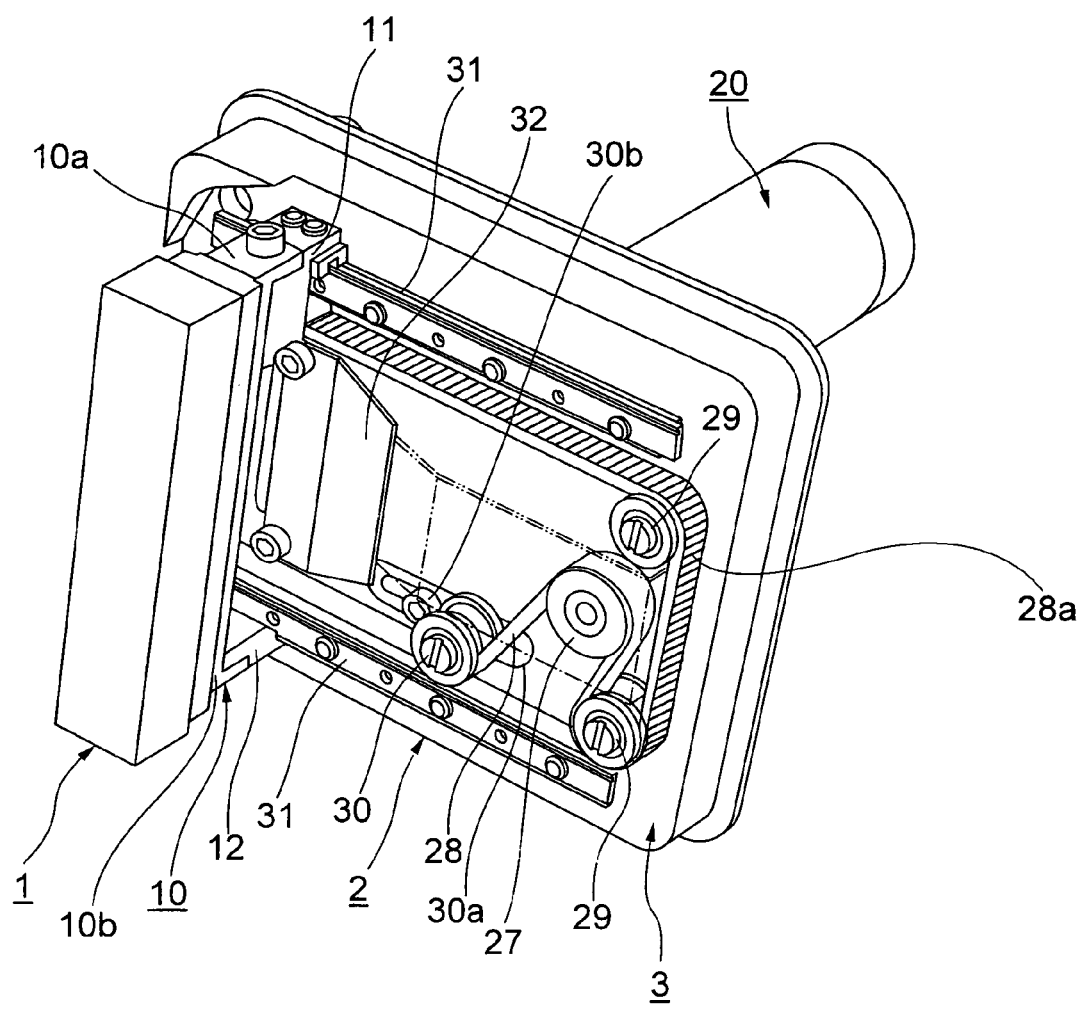
FIG. 1 is a perspective view of a piezoelectric element group (probe main body) of an ultrasonic probe of the present invention, and a movement mechanism that linearly reciprocates this probe main body in a minor axis direction, seen from the front side (where a cover that covers a container main body is removed).

FIG. 1 is a perspective view of a piezoelectric element group (hereunder, referred to as "probe main body") of an ultrasonic probe of the present invention, and a movement mechanism that linearly moves this probe main body in the minor axis direction. Here, as with the conventional example, a cover is placed on and seals a container main body that houses the probe main body, and the inside of the sealed container is filled with oil that functions as an ultrasonic medium. However, this cover and oil are omitted in FIG. 1 in order to facilitate the description of the embodiment of the present invention. In particular, a minor axis mechanical scanning probe that is an embodiment of the ultrasonic probe of the present invention is such that, as shown in FIG. 1, there are provided; a probe main body 1, a movement mechanism 2 that linearly and mechanically reciprocates the probe main body 1 in the minor axis direction, and a container main body 3 to which this movement mechanism 2 is attached (a cover (not shown in the drawing) is fitted on and seals this container main body 3 so as to form a sealed container, and this sealed space is filled with oil that functions as an ultrasonic medium). Furthermore, as shown in FIG. 2, which is a perspective view of the ultrasonic probe of the present invention seen from the rear side thereof, on the back side of the container main body 2 there is provided an electric motor 20 such as DC motor or a step motor that serves as an drive source for linearly reciprocating the movement mechanism 2 in the minor axis direction.

Figure 9A:
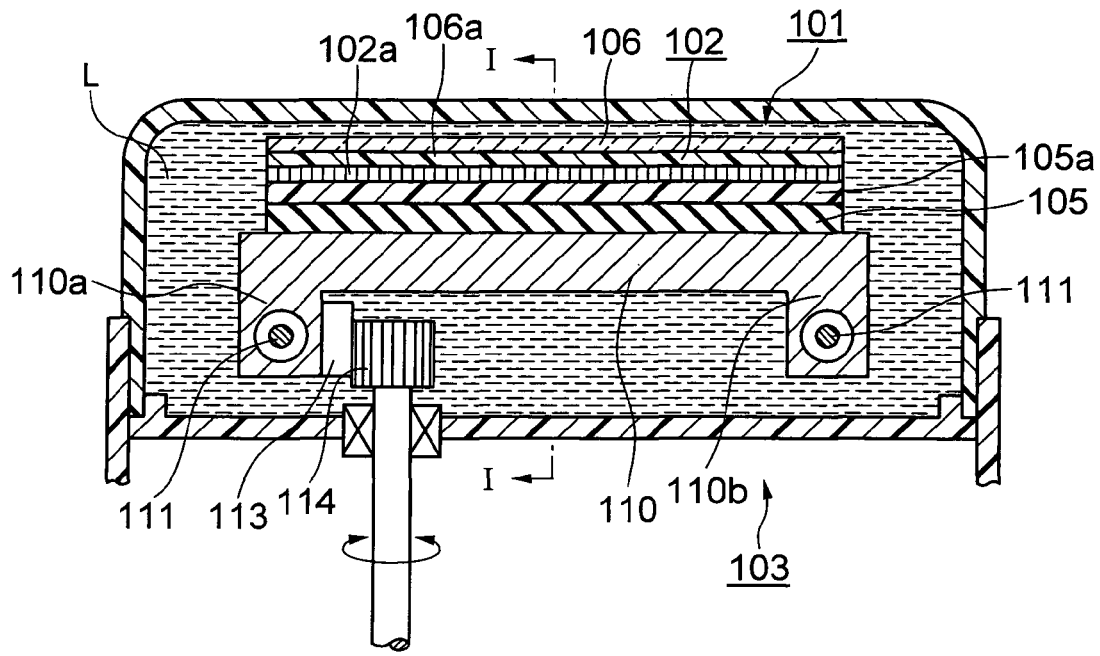
FIG. 9A shows a major axis direction view of a conventional minor axis mechanical scanning probe.
Figure 9B:
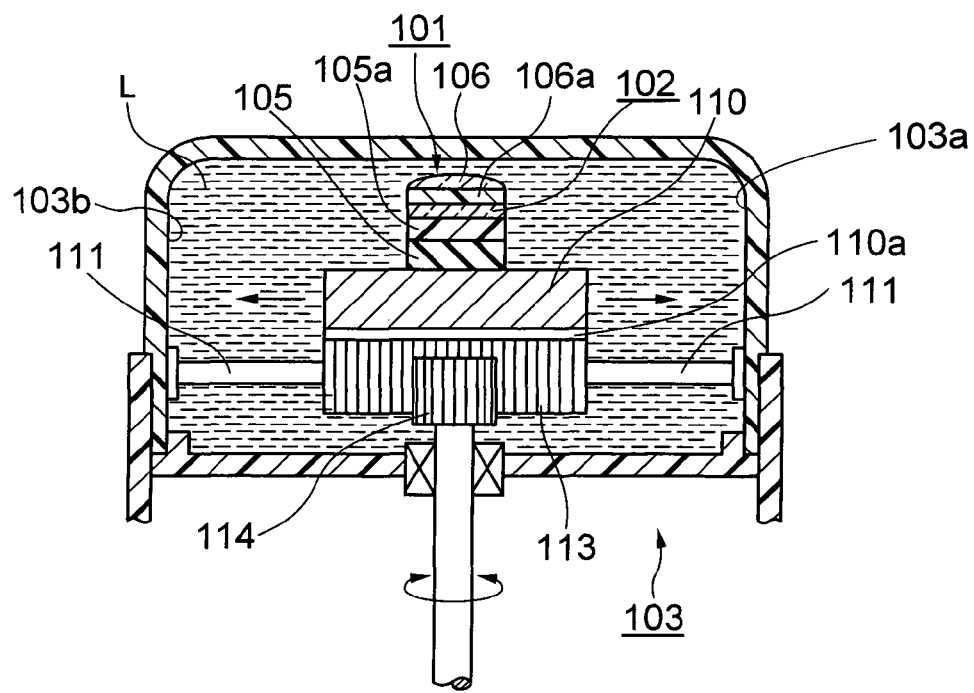
FIG. 9B shows a minor axis direction sectional view of the same minor axis mechanical scanning probe (sectional view taken along the line I-I in FIG. 9A).

The probe main body 1 that constitutes the ultrasonic probe of the present invention is of a configuration the same as that of the conventional probe main body shown in FIGS. 9A and 9B, and has a piezoelectric element group 102 comprising a plurality of strip shaped piezoelectric elements 102a arranged in a line and in a flat shape (on a plane) in the major axis direction, which is the crosswise direction of the piezoelectric elements 102a. The piezoelectric element group 102 is fixed on a backing member 105a of a flat plate shaped base 105, and the base 105 is fixed on a movable mount 10 (refer to FIG. 1). Furthermore, on the ultrasonic wave transmitting/receiving surface of the piezoelectric element group 102 there is provided an acoustic matching layer 106a, and an acoustic lens 106 having a predetermined curvature (convex) in the minor axis direction is provided thereon.

Moreover, the above mentioned piezoelectric element group 102 may comprise a first piezoelectric element group and a second piezoelectric element group, and these may be arranged in a row arrangement in the major axis direction. In this embodiment, the ultrasonic wave frequencies of the first piezoelectric element group and the second piezoelectric element group are different from each other. The ultrasonic wave frequency of the first piezoelectric element group is 7.5 MHz and that of the second piezoelectric element group is 10 MHz. In such a probe, when diagnosing a deep section of a breast for example, a piezoelectric element of a low ultrasonic wave frequency (7.5 MHz) is used, and when diagnosing a shallow section in proximity to the surface of a living body, a piezoelectric element of a high ultrasonic wave frequency (10 MHz) is used. In this embodiment, by means of a switching mechanism of an electric circuit (not shown in the drawing), an electric pulse supply to the first piezoelectric element group or the second piezoelectric element group is switched to either one.

Figure 2:
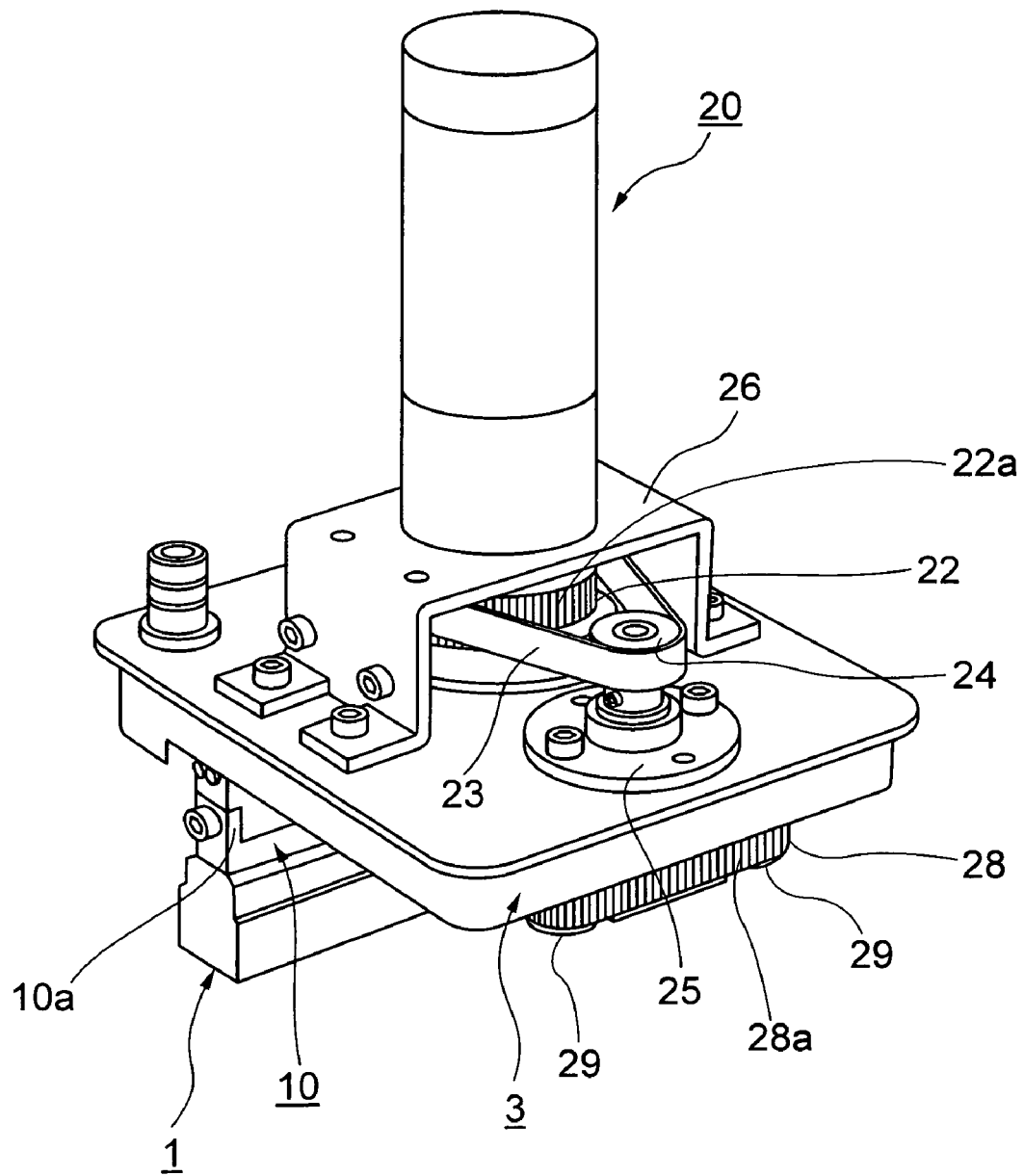
FIG. 2 is a perspective view of the ultrasonic probe of the present invention shown in FIG. 1 seen from the rear side thereof, showing a driving part of the movement mechanism.

On the other hand, the electric motor 20 that serves as a drive source for linearly reciprocating the probe main body 1 in the minor axis direction is fixed, as shown in FIG. 2, on the back surface of the container main body 3 via a bracket 26. A rotational drive force of this motor 20 is transmitted, by a driving pulley 22 that is fitted on the output shaft of this electric motor 20 and that has a toothed section 22a formed on the outer circumference thereof, and a second endless timing belt 23 that is meshed with the toothed section 22a of the driving pulley 22, via a flanged driven pulley supported on a bearing stand 25, and by the second endless timing belt (another endless belt) 23 that drives (rotates) this driven pulley 24.

Here, the electric motor 20 is capable of forward/reverse rotation, and on the output shaft side thereof there is built-in a speed reducer (not shown in the drawing), and on the other end side thereof there is built-in an encoder.

Furthermore, on the other end side of the rotation shaft of the driven pulley 24 shown in FIG. 2 (on the front side of the container main body 3), as shown in FIG. 1 there is fitted a flanged timing pulley 27 having a toothed section 27*a* on its outer circumference, and a first endless timing belt (endless belt) 28 having a toothed section 28*b* on its outside surface is wrapped about, for example, four idle pulleys 29 rotatably journalled in four corners on the front side surface of the container main body 3, and the above timing pulley 27.

In particular, the linear movement mechanism 2 of the probe main body 1 of the ultrasonic probe of the present invention, is configured such that the toothed section 28*a* formed on the outer side of the timing belt 28 engages with the toothed section 27*a* formed on the outer circumference of the timing pulley 27 so that the rotational force of the electric motor 20 is reliably transmitted to the timing belt 28, thereby reciprocating the timing belt 28 in the linear direction.

On the other hand, the four idle pulleys 29 installed in the four corners of the container main body 3 are in contact with the inner side (where there is no toothed section formed) of the timing belt 28. Therefore, they simply move freely and rotate, and function to guide the reciprocation of the timing belt 28. Here, between the timing pulley 27 and the idle pulleys 29, as clearly shown in FIG. 3, there is provided a tension pulley 30. By loosening an adjusting screw 30*b* and moving the shaft of the tension pulley 30 in the minor axis direction within a long hole 30*a*, the tension force (tension) applied to the timing belt 28 can be adjusted.

Figure 3:
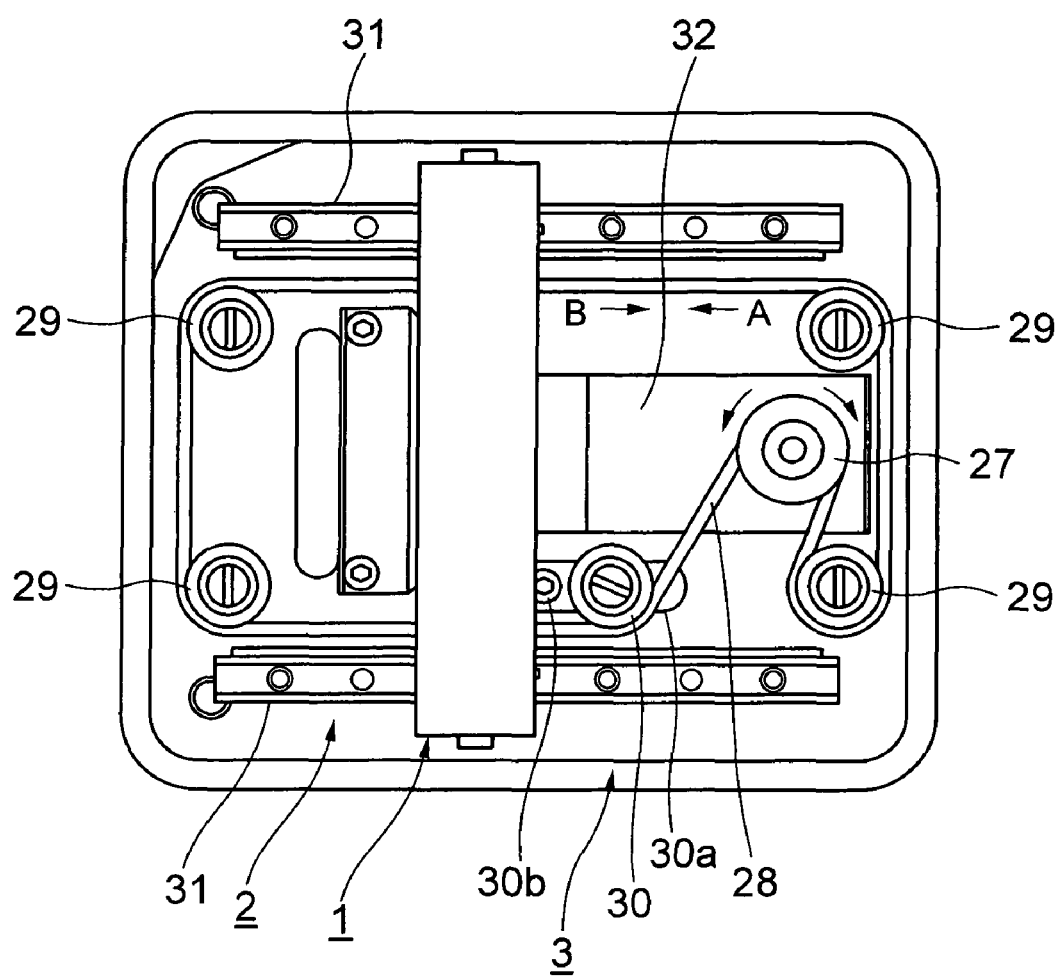
FIG. 3 shows a plan view of the movement mechanism of the ultrasonic probe of the present invention shown in FIG. 1.
Figure 4:
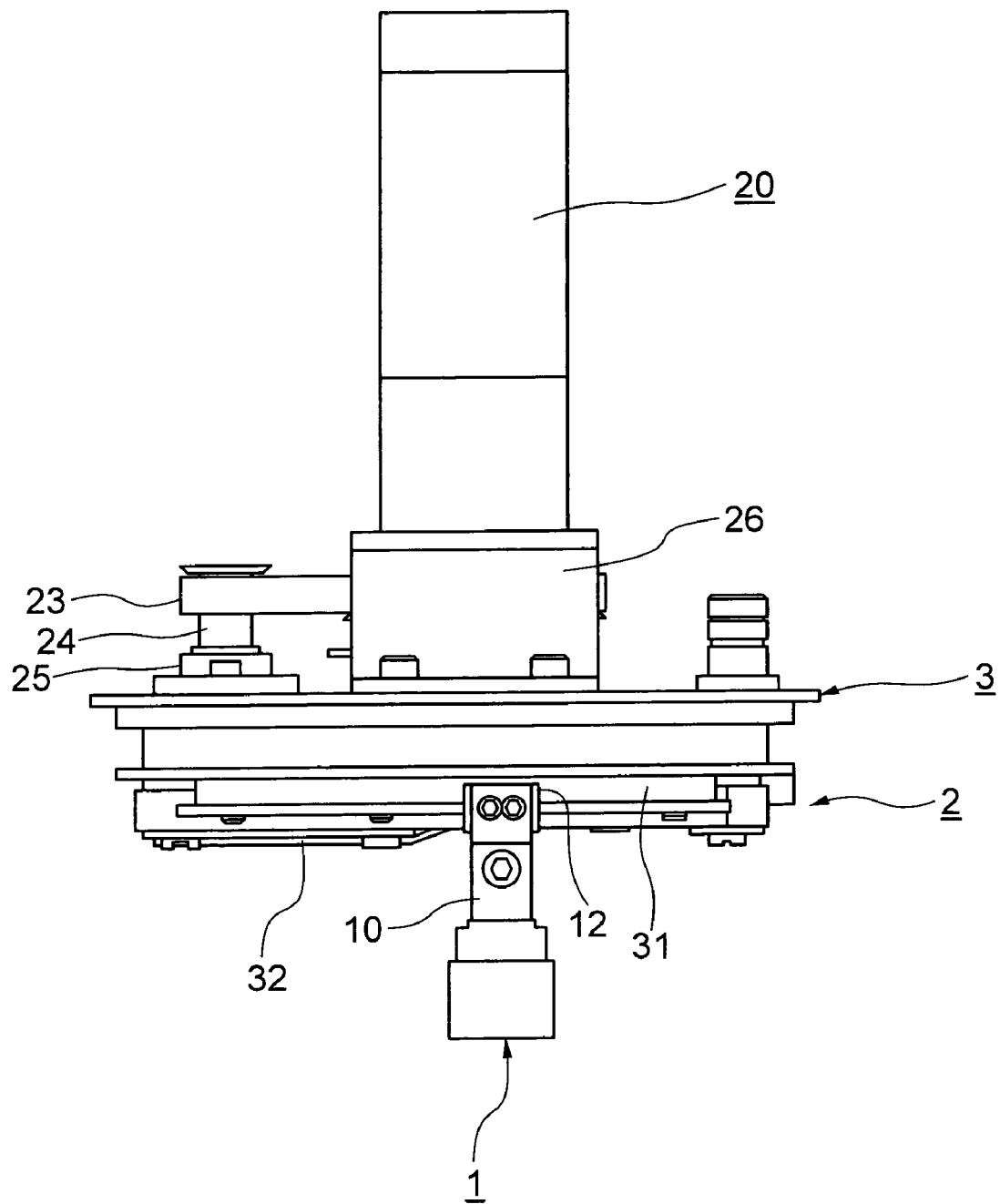
FIG. 4 shows a front view of the same movement mechanism.
Figure 5:
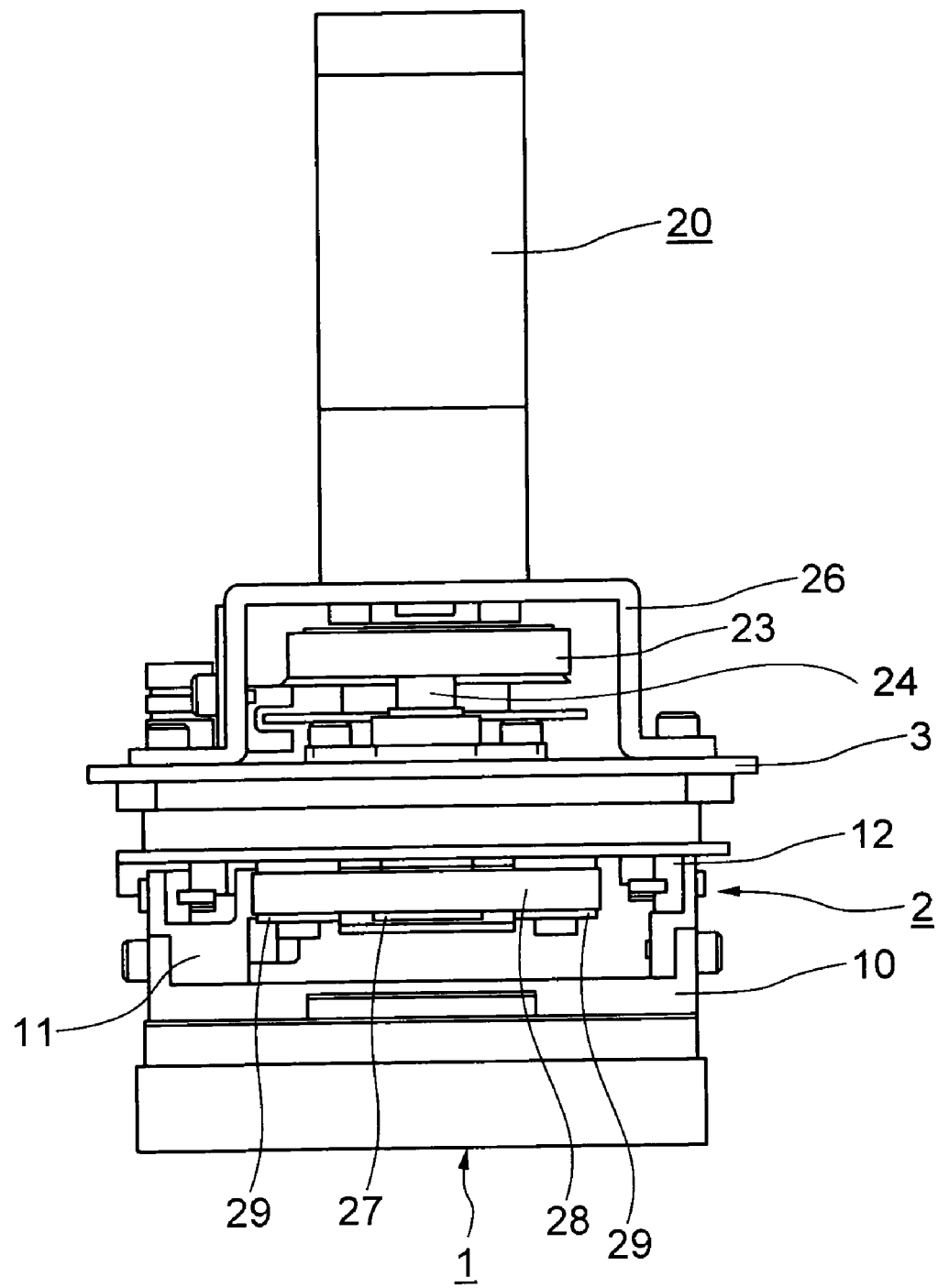
FIG. 5 shows a side view of the same movement mechanism.
Figure 6:
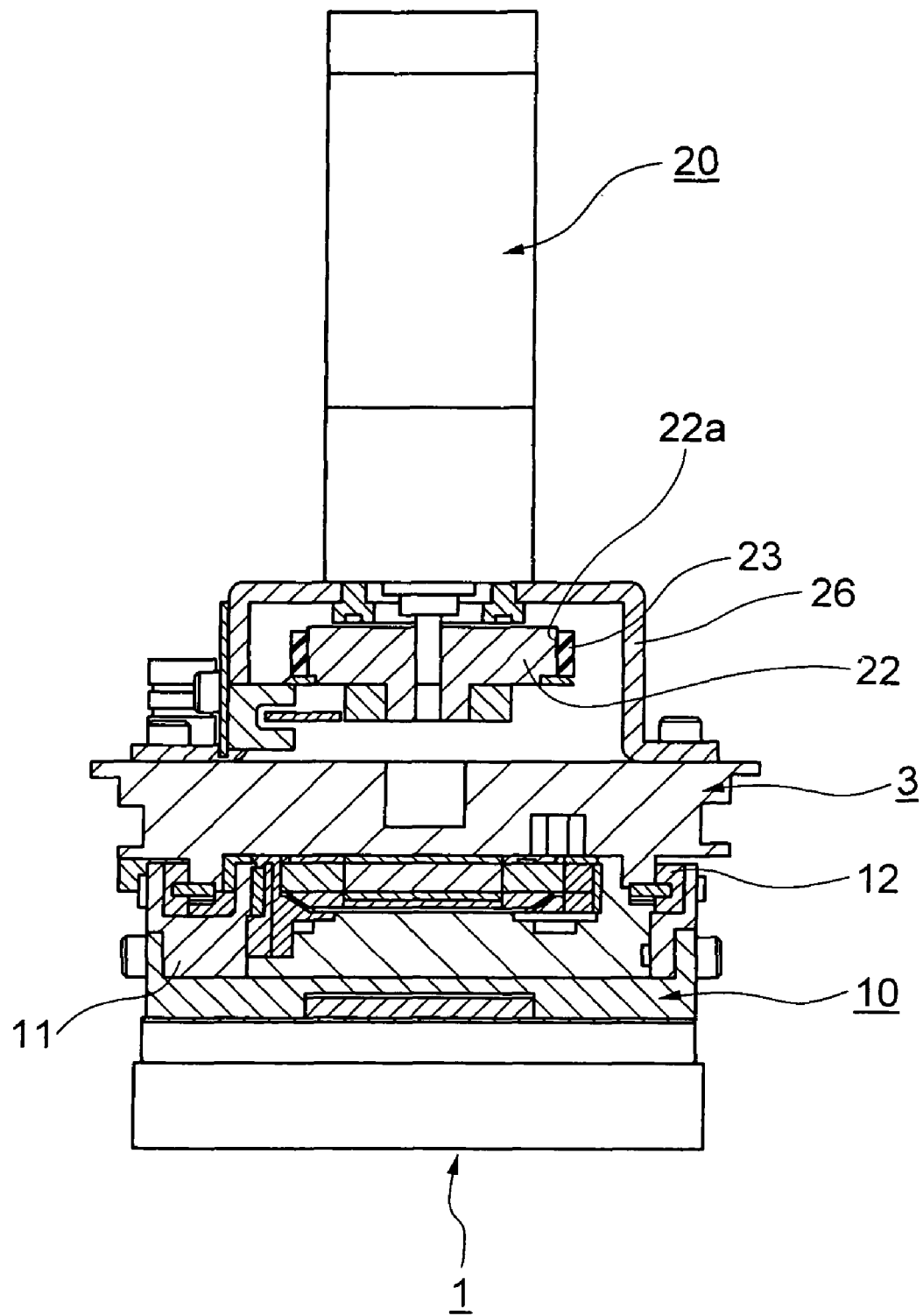
FIG. 6 shows a cross-sectional view (in the major axis direction) of the same movement mechanism.
Figure 7:
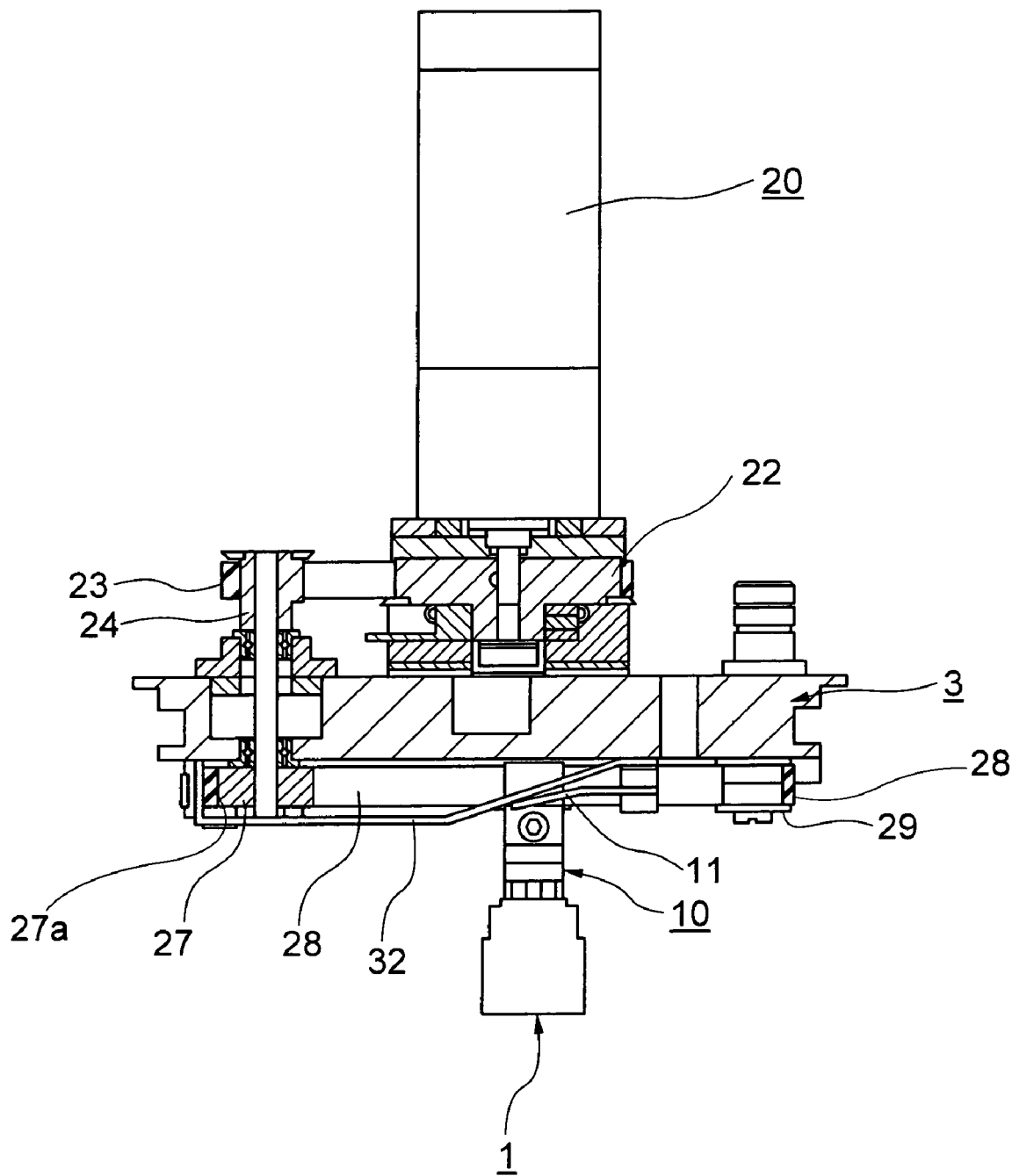
FIG. 7 shows a longitudinal sectional view (in the minor axis direction) of the same movement mechanism.

Furthermore, as shown in FIG. 1 and FIG. 3; a pair of linear guides 31 is provided in a row arrangement and screwed on the front side surface of the container main body 3, the movable mount 10 is fixed to the bottom section (base 105 shown in FIG. 9) of the probe main body 1, and a tightening member 11 is installed on an upper leg section 10*a* of the movable mount 10, to thereby hold (fix) the timing belt 28. Together with this, the leg section 10*a* is guided on one of the linear guides 31 enabling reciprocation in the linear (minor axis) direction.

Moreover, on the other lower leg section 10*b* of the movable mount 10 there is fixed a guide member 12 (not fixed to the timing belt 28), and the leg section 10*b* of the movable mount 10 is guided on the other linear guide 31, similarly enabling reciprocation in the linear direction. This guide member 12 does not hold (fix) the timing belt 28.

Furthermore, on the inner side of the timing belt 28, as shown in FIG. 1, there is provided a plexible substrate cover 32 to prevent a conductive plexible substrate (not shown in the drawing) that conducts electricity to the piezoelectric element group 102, from becoming caught in the movable sections such as the timing belt 28.

In FIG. 1, the plexible substrate cover 32 is partially shown with broken chain lines so that it does not obstruct viewing of other members in the drawing.

With such a configuration, as shown in FIG. 3, in the ultrasonic probe of the present invention, the first timing belt 28 is such that the toothed section 28*a* thereof engages with the toothed section 27*a* of the timing pulley 27, and the inner surface thereof (flat section where there is no toothed section provided) moves freely in contact with and wrapped about the four idle pulleys 29 arranged in between the pair of linear guides 31. At the same time, an appropriate tension force (tension) is applied to the inner surface by the tension pulley 30. As a result the rotational force of the electric motor 20 is reliably transmitted to the first timing belt 28.

Figure 8A:
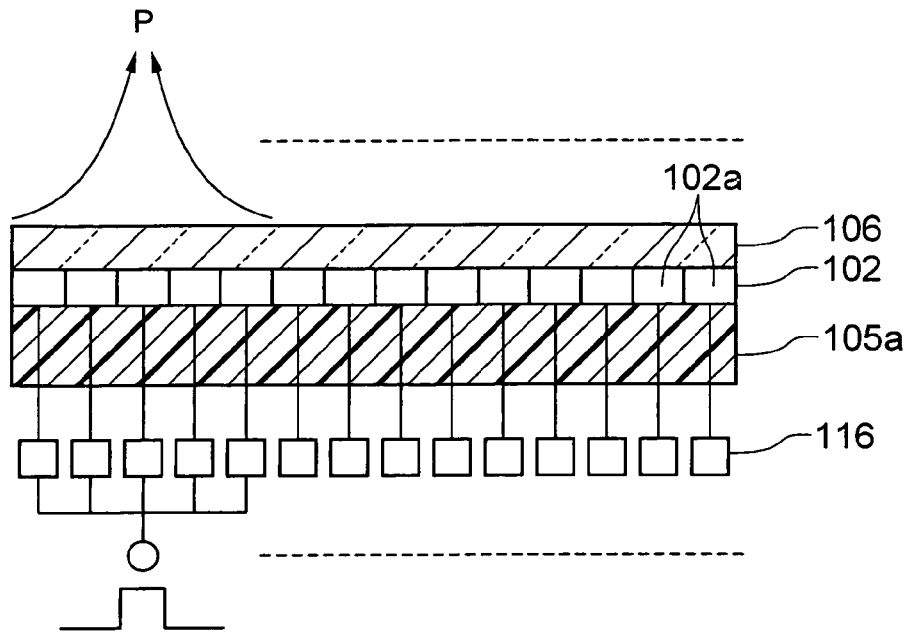
FIG. 8A shows a schematic diagram that illustrates a state where a pulse is being applied to first five piezoelectric elements via a delay circuit.
Figure 8B:
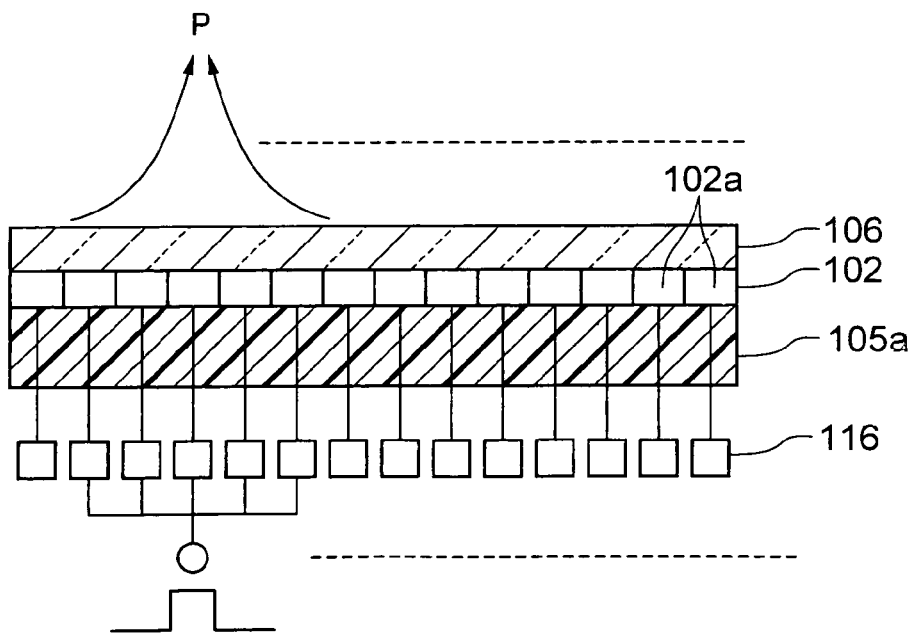
FIG. 8B shows a schematic diagram that illustrates a state where a pulse is being applied to the next switched five piezoelectric elements.

In the ultrasonic probe of the present invention, in the major axis direction thereof, as shown in FIGS. 8A and 8B for example, pulses are applied via delay circuits 116 from one end side of the piezoelectric element group 102 to a plurality, for example five, of the piezoelectric elements 102*a*, and these pulses are electronically converged. Then, the piezoelectric elements 102*a* are switched to the next five piezoelectric elements 102*a*, and similar pulses are applied to the piezoelectric elements 102*a*. This is repeated in sequence, and as shown by the dotted lines, ultrasonic waves P are converged to perform linear scanning in the major axis direction. With this scanning, the contact main body 1 is mechanically linear-scanned in the minor axis direction by the movement mechanism 2. Moreover the contact main body 1 is electronically linear-scanned in the major axis direction, thereby enabling acquisition of a three dimensional image of a living body. Here, on the surface of the piezoelectric element group 102 there is provided an acoustic lens 106, and on the undersurface thereof there is provided the backing member 105*a*.

Next, the operation of the ultrasonic probe of the present invention configured in the above manner is described.

First, when the electric motor 20 shown in FIG. 1 is rotation-driven (for example, forward rotation, clockwise direction rotation), the rotational force of the electric motor 20 is reduced to a predetermined rotation speed by the speed reducer built into the electric motor 20, and transmitted to the driving pulley 22 shown in FIG. 2, and is then transmitted to the driven pulley 24 connected, via the second timing belt 23, to this driving pulley 22. As mentioned above, the timing pulley 27 shown in FIG. 1 is concentric with the above output shaft of the driven pulley 24. Therefore the first timing belt 28 meshed with the toothed section 27*a* of the timing pulley 27 is guided by the four idle pulleys 29 and moved in the direction shown by arrow A in FIG. 3. With this movement, since the probe main body 1 is fixed on the timing belt 28 by the tightening member 11 as shown in FIG. 1, it is linearly moved similarly along the pair of linear guides 31 in the direction of the arrow A (minor axis direction), and pulses are applied and ultrasonic waves P are converged to perform linear scanning in the minor axis direction within a constant speed range (a speed range in which the rotation speed returns to the normal rotation speed after the rotation speed of the electric motor 20 has become zero with forward/reverse rotation).

On the other hand, when the electric motor 20 shown in FIG. 1 is reverse-rotated (counter clockwise direction rotation), the rotational force of the electric motor 20 is similarly transmitted to the driving pulley 22 shown in FIG. 2, and it is then transmitted to the driven pulley 24 connected, via the timing belt 23, to this driving pulley 22. As mentioned above, the timing pulley 27 shown in FIG. 1 is concentric with the above output shaft of the driven pulley 24. Therefore, the first timing belt 28 meshed with the toothed section 27*a* of the timing belt 27 is guided by the four idle pulleys 29 and moved in the direction shown by arrow B in FIG. 3. With this movement, the probe main body 1 similarly moves along the pair of linear guides 31 in the direction of the arrow B. As a result, the probe main body 1 can linearly reciprocate in the minor axis direction. Then, pulses are applied similarly within the constant speed range, to perform linear scanning in the minor axis direction (reverse direction).

Moreover, control of forward/reverse rotation and rotation speed of the electric motor 20 is automatically performed by the encoder built into the electric motor 20. In the ultrasonic probe of the present invention, linear movement of the probe main body 1 in the minor axis direction is possible up to the immediate vicinity of the inner walls of the sealed container. Therefore, movement of the probe main body in the minor axis direction to the fullest extent is guaranteed, and sufficient movement stroke can be ensured.

The ultrasonic probe of the present invention can be widely used for forming a three dimensional image of a body to be examined such as a living body.

What is claimed is:

1. An ultrasonic probe, comprising:
    a container main body member having a front surface and back surface;
    a probe main body extending from the front surface of the container main body, the probe main body including a flat shaped piezoelectric element group having a plurality of strip shaped piezoelectric elements arranged along a major axis direction formed and housed within the container main body, wherein said probe main body is configured and adapted to be mechanically scanned in a minor axis direction substantially orthogonal to said major axis direction;
    a first endless belt having a toothed section on one surface thereof configured and adapted to linearly reciprocate and mechanically scan said probe main body along said minor axis direction;
        a drive source configured and adapted to drive said first endless belt, said drive source including:
            an electric motor capable of forward and reverse rotation;
            a driving pulley engaged with an output shaft of said electric motor;
            a second endless belt connected to said driving pulley;
            a driven pulley coupled to said second endless belt such that rotational movement of said driving pulley causes rotational movement of said driven pulley via said second endless belt; and
            a timing pulley connected to said driven pulley; and
    a pair of linear guides provided in a row arrangement with a predetermined space therebetween along said major axis direction on said front side surface of said container main body whereby said probe main body is guided by said linear guides while reciprocating along said minor axis direction wherein said toothed section of said first endless belt is meshed with a corresponding toothed section of said timing pulley whereby said timing pulley is connected to said drive source for reciprocating said first endless belt and said probe main body along the minor axis direction; wherein the drive source is positioned on the back surface of the container main body, and the first and second endless belts are positioned in parallel along the front and back surfaces of the container main body, respectively.

2. An ultrasonic probe according to claim 1, wherein said first endless belt reciprocates in the minor axis direction and freely moves while being in contact with respective outer circumferential surfaces of a plurality of idle pulleys rotatably journalled on said front surface of said container main body.

3. An ultrasonic probe according to claim 2, wherein, between said timing pulley and said idle pulleys, there is arranged a tension pulley, and said tension pulley is configured and adapted for positioning in the minor axis direction for adjustment of a tension force on said first endless belt.

4. An ultrasonic probe according to claim 1, further including:
    a movable mount fixed on a bottom face of said probe main body;
    a leg section provided on an upper end section of said movable mount;
    a tightening member fixed on said leg section to hold said first endless belt; and
    a guide member fixed on a lower end section of said movable mount; wherein said probe main body is configured and adapted to slide slid on said pair of linear guides integrally with said first endless belt and reciprocated in the minor axis direction.

5. An ultrasonic probe according to claim 1, wherein said piezoelectric element group of said probe main body includes a first piezoelectric element group and a second piezoelectric element group respectively having different ultrasonic wave frequencies, and said first piezoelectric element group and said second piezoelectric element group are provided in a row arrangement in the major axis direction.

6. An ultrasonic probe according to claim 1, wherein said ultrasonic probe is a minor axis scanning type ultrasonic probe.

* * * * *